(12) United States Patent
Snyder et al.

(10) Patent No.: US 10,939,895 B2
(45) Date of Patent: Mar. 9, 2021

(54) STEADY FRAME RATE VOLUMETRIC ULTRASOUND IMAGING

(71) Applicant: KONINKLIJKE PHILIPS N.V., Eindhoven (NL)

(72) Inventors: Richard Allen Snyder, Chester, NH (US); Chicheong Stephen So, Wakefield, MA (US); Martin James Moynihan, Andover, MA (US); Lars Jonas Olsson, Woodinville, WA (US); Lynette May Ward, Newburyport, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 813 days.

(21) Appl. No.: 14/356,182

(22) PCT Filed: Nov. 1, 2012

(86) PCT No.: PCT/IB2012/056088
§ 371 (c)(1),
(2) Date: May 5, 2014

(87) PCT Pub. No.: WO2013/068894
PCT Pub. Date: May 16, 2013

(65) Prior Publication Data
US 2014/0358006 A1   Dec. 4, 2014

Related U.S. Application Data

(60) Provisional application No. 61/557,955, filed on Nov. 10, 2011.

(51) Int. Cl.
*A61B 8/08* (2006.01)
*A61B 8/00* (2006.01)
(Continued)

(52) U.S. Cl.
CPC ............ *A61B 8/483* (2013.01); *A61B 8/0883* (2013.01); *A61B 8/54* (2013.01); *G01S 7/52085* (2013.01); *G01S 15/8993* (2013.01); *G10K 11/34* (2013.01)

(58) Field of Classification Search
CPC ......... A61B 8/483; A61B 8/0883; A61B 8/54; G01S 7/52085; G01S 15/8993; G10K 11/34
See application file for complete search history.

(56) References Cited

U.S. PATENT DOCUMENTS 5,793,701 A   8/1998   Wright et al.
5,967,985 A * 10/1999   Hayakawa ........... A61B 8/0833
                                              600/440
(Continued)

FOREIGN PATENT DOCUMENTS

JP   H04152939 A   5/1992
JP      9192130 A   7/1997
WO   2005034760 A1   4/2005

*Primary Examiner* — Jeffrey G Hoekstra
*Assistant Examiner* — Katherine M McDonald

(57) ABSTRACT

The present invention relates to a method for providing three-dimensional ultrasound images of a volume (50) and an ultrasound imaging system (10). In particular, the current invention applies to live three-dimensional imaging. To maintain a steady frame rate of the displayed images even if a user changes a region of interest and, therewith, the size of the volume (50) to be scanned, it is contemplated to adjust a density of the scanning lines within the volume (50) as a function of a size of the volume while maintaining a total number of scanning lines across the volume (50).

12 Claims, 5 Drawing Sheets

(51) Int. Cl.
  *G01S 7/52* (2006.01)
  *G10K 11/34* (2006.01)
  *G01S 15/89* (2006.01)

(56) References Cited

U.S. PATENT DOCUMENTS

| | | |
|---|---|---|
| 6,494,838 B2 | 12/2002 | Cooley et al. |
| 7,529,393 B2 | 5/2009 | Peszynski et al. |
| 8,366,621 B2 * | 2/2013 | Gunji .................. A61B 8/0883 |
| | | 600/437 |
| 2002/0007680 A1 | 1/2002 | Wiesauer |
| 2003/0018264 A1 | 1/2003 | Suzuki et al. |
| 2004/0187582 A1 | 9/2004 | Satoh |
| 2005/0228280 A1 | 10/2005 | Ustuner et al. |
| 2007/0007680 A1 | 1/2007 | Wiesauer |
| 2007/0078342 A1 | 4/2007 | Jago |
| 2007/0088213 A1 | 4/2007 | Poland |
| 2007/0123110 A1 * | 5/2007 | Schwartz ................ A61B 8/14 |
| | | 439/638 |
| 2007/0276236 A1 * | 11/2007 | Jong ........................ A61B 8/00 |
| | | 600/437 |
| 2008/0087089 A1 | 4/2008 | Nam |
| 2008/0089571 A1 | 4/2008 | Kurita |
| 2009/0203996 A1 | 8/2009 | Thiele et al. |
| 2010/0010352 A1 | 1/2010 | Jong |

\* cited by examiner

STEADY FRAME RATE VOLUMETRIC ULTRASOUND IMAGING

CROSS-REFERENCE TO PRIOR APPLICATIONS

This application is the U.S. National Phase application under 35 U.S.C. § 371 of International Application No. PCT/IB2012/056088, filed on Nov. 1, 2012, which claims the benefit of U.S. Provisional Application No. 61/557,955, filed on Nov. 10, 2011. These applications are hereby incorporated by reference herein.

FIELD OF THE INVENTION

The present invention relates to an ultrasound system and method for providing a live three-dimensional image of a volume, for example an anatomical site of a patient. The present invention further relates to a computer program for implementing such method.

BACKGROUND OF THE INVENTION

In three-dimensional ultrasound imaging, or volume imaging, the acquisition of a three-dimensional image is accomplished by conducting many two-dimensional scans that slice through the volume of interest. Hence, a multitude of two-dimensional images is acquired that lie next to another. By proper image processing, a three-dimensional image of the volume of interest can be built out of the multitude of two-dimensional images. The three-dimensional information acquired from the multitude of two-dimensional images is displayed in proper form on a display for the user of the ultrasound system.

Further, so-called live three-dimensional imaging, or 4D imaging, is often used in clinical applications. In live three-dimensional imaging, a real-time view on the volume can be acquired enabling a user to view moving parts of the anatomical site, for example a beating heart or else. In the clinical application of live three-dimensional imaging there is sometimes a need to image a relatively small area of the heart such as a single valve, or a septal defect, and there is sometimes the need to image a large area of the heart such as an entire ventricle.

Hence, the so-called region of interest (ROI) and its size might change through a clinical application of live three-dimensional ultrasound imaging.

In conventional praxis, the so-called line density, that is a dimension of the volume divided by the total number of scanning lines, specifically the receive scanning lines of a transducer array, is fixed. The line density is also a measure for the space between two adjacent scanning lines. Typically, the line density is expressed as a dimensional value per line, for example in degrees per line. In the case of a fixed line density, the acquisition rate of the volume changes as the region of interest is changed by a user. Larger volumes require more scanning lines or acoustic lines and, thus, the volume rate drops. However, in live three-dimensional imaging, the acquisition rate should be sufficiently high, that is larger than 20 Hz, in particular larger than 24 Hz, to provide a live and moving image. Hence, there is often provided a control for the user to change the line density to compensate for the drop of the acquisition rate. But this is a manual step that can be cumbersome and time-consuming for the user.

Therefore, methods for automatically changing the line density have been contemplated. The reference US 2008/0089571 A1 discloses an ultrasonic probe to scan a three-dimensional region using ultrasonic beams by raising the scanning line density of the transmission of ultrasonic beams for a region of interest compared to the scanning line density of the transmission of ultrasonic beams for regions other than the region of interest among three-dimensional regions.

There is a need to further improve such three-dimensional ultrasound systems.

SUMMARY OF THE INVENTION

It is an object of the present invention to provide an improved ultrasound system and method. It is a further object of the present invention to provide a computer program for implementing such method.

In a first aspect of the present invention, an ultrasound imaging system for providing a three-dimensional image of a volume is presented. The ultrasound imaging system comprises a transducer array configured to provide an ultrasound receive signal, a beam former configured to control the transducer array to scan the volume along a multitude of scanning lines, and further configured to receive the ultrasound receive signal and to provide an image signal, a controller for controlling the beam former, wherein the controller is configured to adjust a density of the scanning lines within the volume as a function of a size of the volume while maintaining a total number of scanning lines across the volume, a signal processor configured to receive the image signal and to provide image data, an image processor configured to receive the image data from the signal processor and to provide display data, and a display configured to receive the display data and to provide the three-dimensional image.

In a further aspect of the present invention a method for providing a three-dimensional ultrasound image of a volume is presented, wherein the volume is to be scanned along a multitude of scanning lines. The method comprises the steps of receiving parameters determining a size of the volume, adjusting a density of the scanning lines as a function of a size of the volume while maintaining a total number of scanning lines across the volume, scanning the volume along the scanning lines with a transducer array providing an ultrasound signal, processing the ultrasound signal to provide image data, and displaying the three-dimensional ultrasound image using the image data.

In a further aspect of the present invention a computer program is presented comprising program code means for causing a computer to carry out the steps of such method when said computer program is carried out on the computer.

The basic idea of the invention is to adjust the line density automatically as a function of the size of the volume or region of interest. By this, a constant and sufficiently high volume acquisition rate can be provided to the user as they change the size of the region of interest to fit their need without any other adjustments. In live three-dimensional imaging there is a need to maintain a sufficiently high volume rate to properly visualize the dynamic nature of the anatomy inspected. When changing between a large region of interest and a small region of interest, there is willingness on the part of the clinician to decrease the image resolution when imaging large regions of interest and to increase the resolution when smaller regions of interest are to be imaged.

Hence, a significant technical benefit of the present invention is that if a size of the region of interest or volume is reduced by the user to image smaller structures, the imaging spatial resolution increases owing to the higher density of the acoustic lines within the region of interest. This is because the total number of scanning lines is kept constant. If the region of interest becomes smaller, the density of the acoustic lines must become higher.

Further, this allows the ultrasound system to maintain high volume acquisition rates across both small and large regions of interest by spreading the scanning lines slicing through the volume as the size of the volume increases, by effectively maintaining a fixed number of acoustic lines or scanning lines and hence a fixed volume acquisition rate. This is regardless of the size of the region of interest.

Preferred embodiments of the invention are defined in the dependent claims. It shall be understood that the claimed method has similar and/or identical preferred embodiments as the claimed device and as defined in the dependent claims.

In one embodiment, the controller is further configured to adjust the density of the scanning lines as a function of a target volume acquisition rate. Hence, a target volume acquisition rate or desired volume acquisition rate is inputted into the controller. In particular, the user might set the target volume acquisition rate to 24 Hz to make sure to being provided with a live three-dimensional image. However, a target acquisition rate for live three-dimensional imaging might also be set automatically, in particular t a value equal or greater than 24 Hz.

Hence, in a further embodiment, the controller is configured to receive the target volume acquisition rate via a user input. By this, a controller is provided to the user which enables the user to choose a target volume acquisition rate to selectively trade-off acquisition rate with imaging spatial resolution as desired. By this, there is achieved a technical effect in that the user may give up live three-dimensional imaging and set a target volume acquisition rate to a lower rate, for example 10 Hz, but with a significantly higher imaging resolution. This is may be of advantage if the user might want to inspect a non-moving or non-dynamic site in the body of the patient with good resolution.

In a further embodiment, the controller is configured to receive the size of the volume in the form of a lateral extent in degrees, an elevation extent in degrees and a depth expressed by a scanning time of each scanning line. By scanning time it is meant the time the ultrasound system spends to acquire or receive an ultrasound echo response image along each scanning line. The scanning time, therefore, is usually inputted in the form of time per line. As scanning time has an effect on the time waited between a sent ultrasound impulse and the answer received by a reflection from the inspected tissue, it is directly proportional to the depth of the volume or region of interest. In particular, the controller is configured to receive the lateral extent and the elevation extent via user input. Hence, the user might vary the lateral extent and the elevation extent to narrow the image acquisition to a smaller region of interest. Further, the controller may be configured to receive the scanning time of each scanning line as a preset or fixed parameter of the ultrasound system. By presetting the scanning time for each scanning line and keeping the total number of scanning lines constant, the ultrasound system is possible to maintain a constant volume acquisition rate during scanning.

In a further embodiment, the controller is further configured to adjust the density of the scanning lines based on the following empirical formula:

$$LD = \sqrt{LE \cdot EE \cdot TVR \cdot LT}$$

wherein LD is the density of the scanning lines in degrees per line, LE is the lateral extent of the volume in degrees, EE is the elevation extent of the volume in degrees, TVR is the target volume rate in Hz and LT is the scanning time of each scanning line in seconds per line. Hertz is the unit measuring cycles per time, i.e. in the current case the unit is 1/seconds. By this, a simple equation is provided that enables the controller to adjust the line density or the spacing between the scanning lines in real time without the need for excess calculation power. Hence, high target acquisition rates for live three-dimensional imaging can be maintained. Further, this equation directly provides for a proportional relationship between the size of the origin of interest and the line density. If the lateral extent or the elevation extent is lowered and, as a result, the size of the volume is reduced, the line density is lowered as well. Further, if the lateral extent or the elevation extent are raised via user input, and, hence, the size of the volume is increased, the line density is increased, and, by this, the ultrasound system is able to maintain the target volume acquisition rate. For example, a user narrows only the lateral extent from 40 degrees to 10 degrees. Hence, the new size of the volume will one fourth of the old size of the volume. Taking into the square root in the formula, the new line density will be half of the old line density. However, the line density has an effect on the spacing of the scanning lines in both the lateral and the elevation direction. Therefore, the number of scanning lines in a given volume will be four times higher. As the new volume has one fourth of the old size, the total number of scanning lines remains constant and, further, the volume acquisition rate remains constant.

In a further embodiment, the controller is further configured to apply a boundary condition on the adjusted density of the scanning lines. By this, it can be secured that the adjusted line density is kept only in a practical range of densities. For example, the boundary condition may be a maximum boundary condition or a maximum line density. For example, given that the total number of acoustic lines is fixed, the maximum line density might be set so that a total number of lines multiplied with the maximum line density does not exceed a maximum angle the transducer array is able to work within. As a further example, the maximum line density might be set to an angle so that the receive beams along adjacent scanning lines do not drift apart too much so that even small objects in a deep position in the volume can still be detected. Additionally or alternatively, the boundary condition may be a minimum boundary condition or a minimum line density. By this, for example, it might be secured that the line density is not lower than a minimum line density or line spacing achievable with a certain transducer array.

In a further embodiment, the controller is further configured to adjust the size of the volume to meet the boundary condition. For example, if the user sets the lateral extent and the elevation extent of the region of interest too large, the controller may override the selection and set some to maximum values instead to meet boundary condition.

In a further embodiment, the controller is configured to adjust an actual volume acquisition rate to meet the boundary condition. However, as the controller shall usually maintain the target volume acquisition rate, this action might be the last measure to meet the boundary conditions. Further, adjusting the actual volume acquisition rate may be combined with the measure of adjusting the size of the volume to meet the boundary condition. In particular, the controller may be configured to lower the actual volume acquisition rate not below 24 Hz to maintain a live three-dimensional imaging under any circumstances. The controller may then start to lower the size of the volume to meet the boundary condition.

BRIEF DESCRIPTION OF THE DRAWINGS

These and other aspects of the invention will be apparent from and elucidated with reference to the embodiment(s) described hereinafter. In the following drawings

FIG. 2b shows a schematic example how a multitude of scanning lines may spread through the volume in FIG. 2a;

FIG. 4b shows another example of a display with a region of interest smaller than that of FIG. 4a.

DETAILED DESCRIPTION OF THE INVENTION

Figure 1:
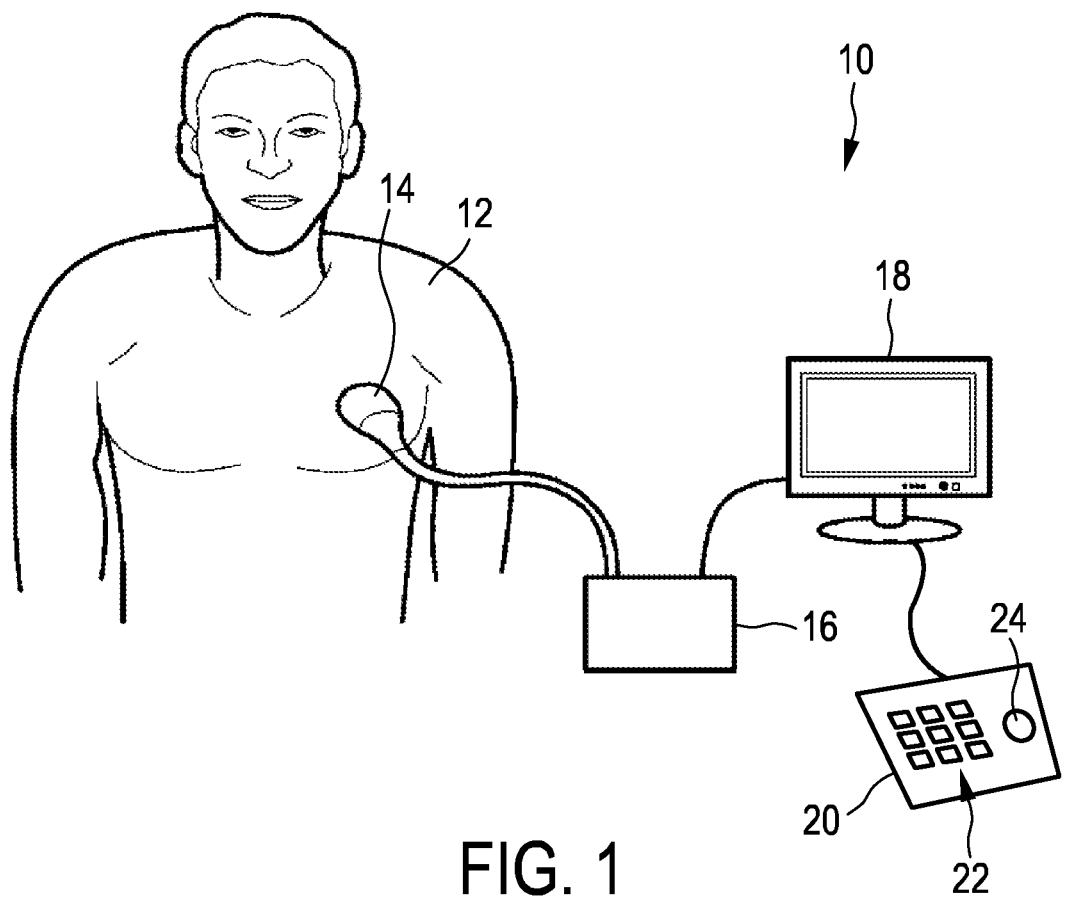
FIG. 1 shows a schematic illustration of an ultrasound system according to an embodiment.

FIG. 1 shows a schematic illustration of an ultrasound system 10 according to an embodiment, in particular a medical ultrasound three-dimensional imaging system. The ultrasound system 10 is applied to inspect a volume of an anatomical site, in particular an anatomical site of a patient 12. The ultrasound system 10 comprises an ultrasound probe 14 having at least one transducer array having a multitude of transducer elements for transmitting and/or receiving ultrasound waves. In one example, the transducer elements each can transmit ultrasound waves in form of at least one transmit impulse of a specific pulse duration, in particular a plurality of subsequent transmit pulses. The transducer elements can for example be arranged in a one-dimensional row, for example for providing a two-dimensional image that can be moved or swiveled around an axis mechanically. Further, the transducer elements may be arranged in a two-dimensional array, in particular for providing a multi-planar or three-dimensional image.

In general, the multitude of two-dimensional images, each along a specific acoustic line or scanning line, in particular scanning receive line, may be obtained in three different ways. First, the user might achieve the multitude of images via manual scanning. In this case, the ultrasound probe may comprise position-sensing devices that can keep track of a location and orientation of the scan lines or scan planes. However, this is currently not contemplated. Second, the transducer may be automatically mechanically scanned within the ultrasound probe. This may be the case if a one dimensional transducer array is used. Third, and preferably, a phased two-dimensional array of transducers is located within the ultrasound probe and the ultrasound beams are electronically scanned. The ultrasound probe may be handheld by the user of the system, for example medical staff or a doctor. The ultrasound probe 14 is applied to the body of the patient 12 so that an image of an anatomical site in the patient 12 is provided.

Further, the ultrasound system 10 has a controlling unit 16 that controls the provision of a three-dimensional image via the ultrasound system 10. As will be explained in further detail below, the controlling unit 16 controls not only the acquisition of data via the transducer array of the ultrasound probe 14 but also signal and image processing that form the three-dimensional images out of the echoes of the ultrasound beams received by the transducer array of the ultrasound probe 14.

The ultrasound system 10 further comprises a display 18 for displaying the three-dimensional images to the user. Further, an input device 20 is provided that may comprise keys or a keyboard 22 and further inputting devices, for example a track ball 24. The input device 20 might be connected to the display 18 or directly to the controlling unit 16.

Figure 2A:
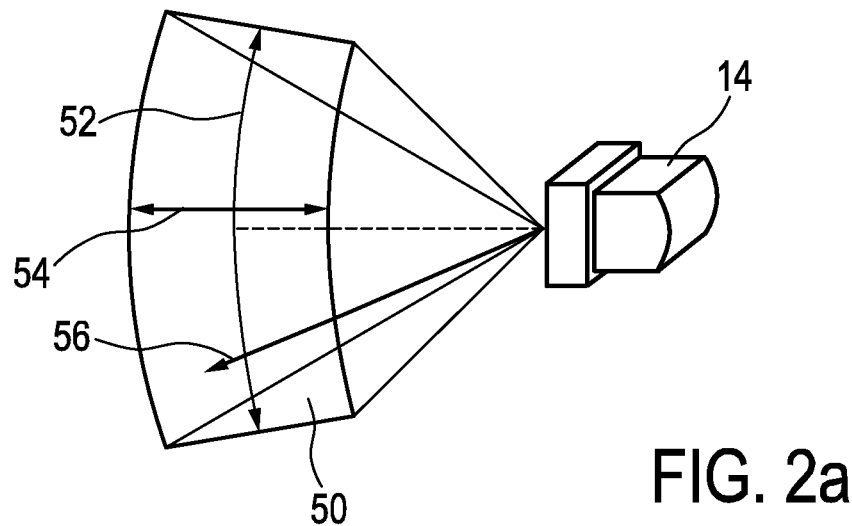
FIG. 2a shows a schematic representation of a region of interest in relation to an ultrasonic probe.

FIG. 2a shows an example of a volume 50 relative to the ultrasound probe 14. The exemplary volume 50 depicted in this example is of a sector type, due to the transducer array of the ultrasound probe 14 being arranged as a phased two-dimensional electronically scanned array. Hence, the size of the volume 50 may be expressed by an elevation angle 52 and a lateral angle 54. A depth 56 of the volume 50 may be expressed by a so-called line time in seconds per line. That is the scanning time spent to scan a specific scanning line.

Figure 2B:
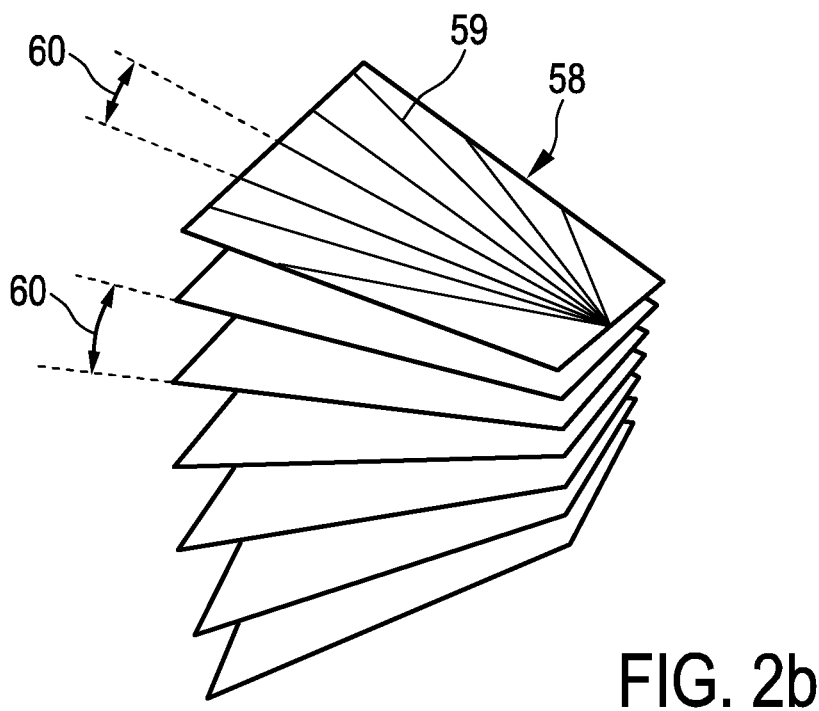

FIG. 2b shows an illustrative example how the volume 50 may be divided into a multitude of slices 58 or two-dimensional images each acquired along a multitude of so-called scan lines 59. During image acquisition, the two-dimensional transducer array of the ultrasound probe 14 is operated by a beam former in a way that the volume 50 is scanned along a multitude of these scan lines 58 sequentially. However, in multi-line receive processing, a single transmit beam might illuminate a multitude, for example four, receive scanning lines along which signals are acquired in parallel. If so, such sets of receive lines are then electronically scanned across the volume 50 sequentially.

Hence, a resolution of a three-dimensional image processed out of the acquired two-dimensional images depends on a so-called line density which in turn depends on a spacing 60 between two adjacent scanning lines 59. In fact, it is the distance between two adjacent scan lines 59 within a slice 58 and, further, between the slices 58. As a result, the line density in the direction of the lateral extent and in the direction of the elevation extent is the same. Hence, the line density is measured in the form of degrees per line.

Figure 3:
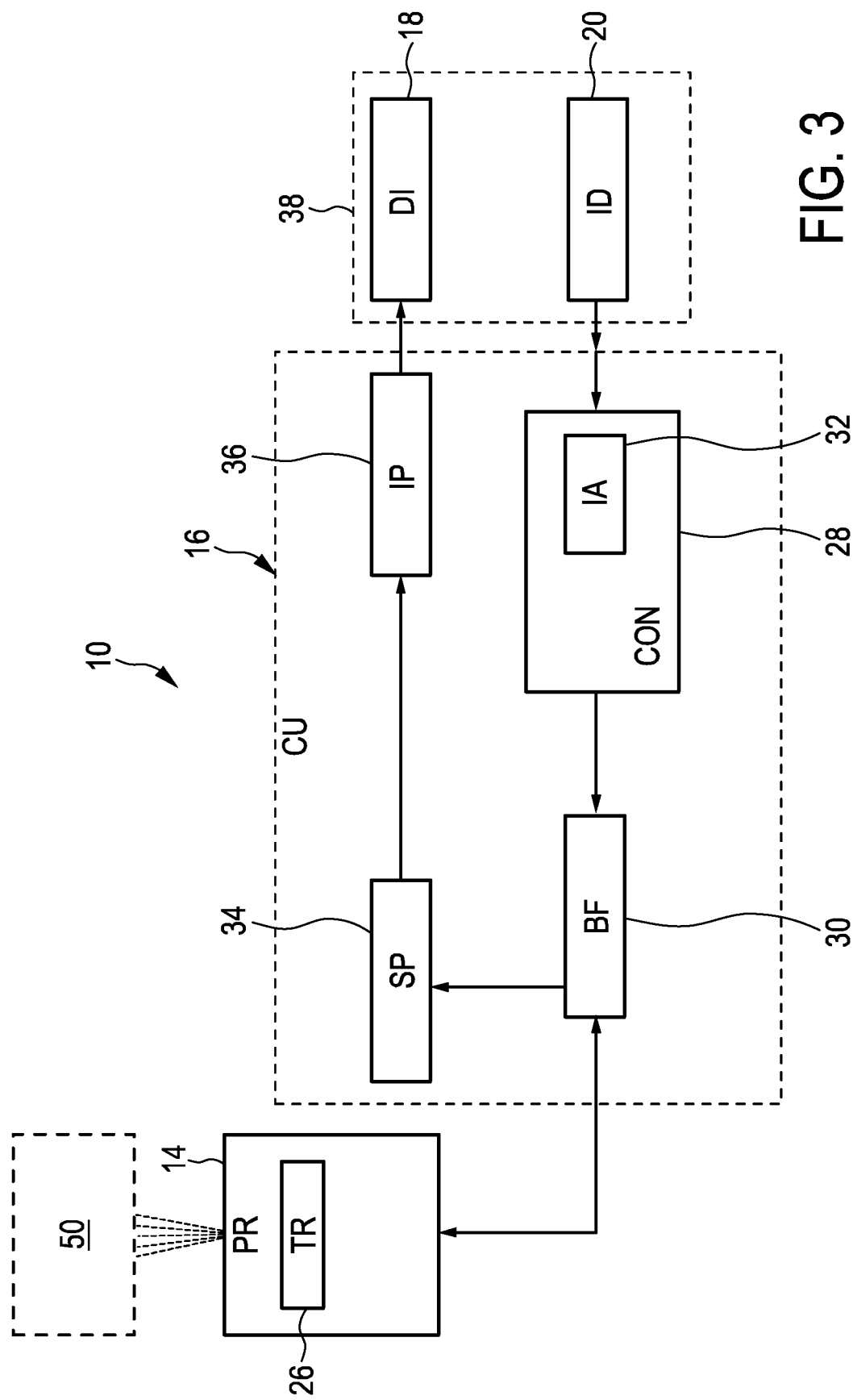
FIG. 3 shows a schematic block diagram of the ultrasound system according to the embodiment.

FIG. 3 shows a schematic block diagram of the ultrasound system 10. As already laid out above, the ultrasound system 10 comprises an ultrasound probe (PR) 14, the controlling unit (CU) 16, the display (DI) 18 and the input device (ID) 20. As further laid out above, the probe 14 comprises a phased two-dimensional transducer array 26. In general, the controlling unit (CU) 16 may comprise a central processing unit that may include analog and/or digital electronic circuits, a processor, microprocessor or the like to coordinate the whole image acquisition and provision. Further, the controlling unit 16 comprises a herein called image acquisition controller 28. However, it has to be understood that the image acquisition controller 28 does not need to be a separate entity or unit within the ultrasound system 10. It can be a part of the controlling unit 16 and generally be hardware or software implemented. The current distinction is made for illustrative purposes only. The image acquisition controller 28 as part of the controlling unit 16 may control a beam former and, by this, what images of the volume 50 are taken and how these images are taken. The beam former 30 generates the voltages that drives the transducer array 26, determines parts repetition frequencies, it may scan, focus and apodize the transmitted beam and the reception or receive beam(s) and may further amplify filter and digitize the echo voltage stream returned by the transducer array 26. Further, a herein called image acquisition part 32 of the image acquisition controller 28 of the controlling unit 16 may determine general scanning strategies. Such general strategies may include a desired volume acquisition rate, lateral extent of the volume, an elevation extent of the volume, maximum and minimum line densities, scanning line times and the line density as already explained above. Again, the image acquisition part 32 does not need to be a separate entity or unit within the ultrasound system 10. It can be a part of the controlling unit 16 and generally be hardware or software implemented. The current distinction is made for illustrative purposes only. The image acquisition part 32 can also be implemented in, for example, the beam former 30 or the general controlling unit 16 or may be implemented as a software run on a data processing unit of the controller 16.

The beam former 30 further receives the ultrasound signals from the transducer array 26 and forwards them as image signals.

Further, the ultrasound system 10 comprises a signal processor 34 that receives the image signals. The signal processor 34 is generally provided for analogue-to-digital-converting, digital filtering, for example, band pass filtering, as well as the detection and compression, for example a dynamic range reduction, of the received ultrasound echoes or image signals. The signal processor forwards image data.

Further, the ultrasound system 10 comprises an image processor 36 that converts image data received from the signal processor 34 into display data finally shown on the display 18. In particular, the image processor 36 receives the image data, preprocesses the image data and may store it in an image memory. These image data is then further post-processed to provide images most convenient to the user via the display 18. In the current case, in particular, the image processor 36 may form the three-dimensional images out of a multitude of two-dimensional images acquired along the multitude of scan lines 59 in each slice 58.

A user interface is generally depicted with reference numeral 38 and comprises the display 18 and the input device 20. It may also comprise further input devices, for example, a mouse or further buttons which may even be provided on the ultrasound probe 14 itself.

A particular example for a three-dimensional ultrasound system which may apply the current invention is the CX50 CompactXtreme Ultrasound system sold by the applicant, in particular together with a X7-2t TEE transducer of the applicant or another transducer using the xMATRIX technology of the applicant. In general, matrix transducer systems as found on Philips iE33 systems or mechanical 3D/4D transducer technology as found, for example, on the Philips iU22 and HD15 systems may apply the current invention.

In use, general system inputs are made as preset or fixed parameters of the ultrasound system 10. These so-called system inputs in particular are a maximum line density, in minimum line density and a scan line time. The user may then input a target volume acquisition rate and, in particular, further specify the size of the volume to be scanned or region of interest in the form of a lateral extent and an elevation extent of the volume 50 to the ultrasound system 10. The user may input the lateral extent and the elevation extent directly as a numeric value, for example, 40 degrees. But, the user may also, for example, select a certain region via the user interface 38 on the display 18 which selection is then translated into numerical values for the lateral extent and elevation extent and forwarded to the image acquisition part 32.

Based on these inputs, the line density is characterized according to the following empirical formula:

$$LD = \sqrt{LE \cdot EE \cdot TVR \cdot LT},$$

wherein LD is the density (60) of the scanning lines (28) in degrees per line, LE is the lateral extent of the volume (50) in degrees, EE is the elevation extent of the volume (50) in degrees, TVR is the target volume acquisition rate in hertz and LT is the scanning time of each scanning line in seconds per line.

For example, the system inputs may be a maximum line density of 3 degrees, a minimum line density of 0.75 degrees and a line time of 0.00005 seconds per line.

Figure 4A:
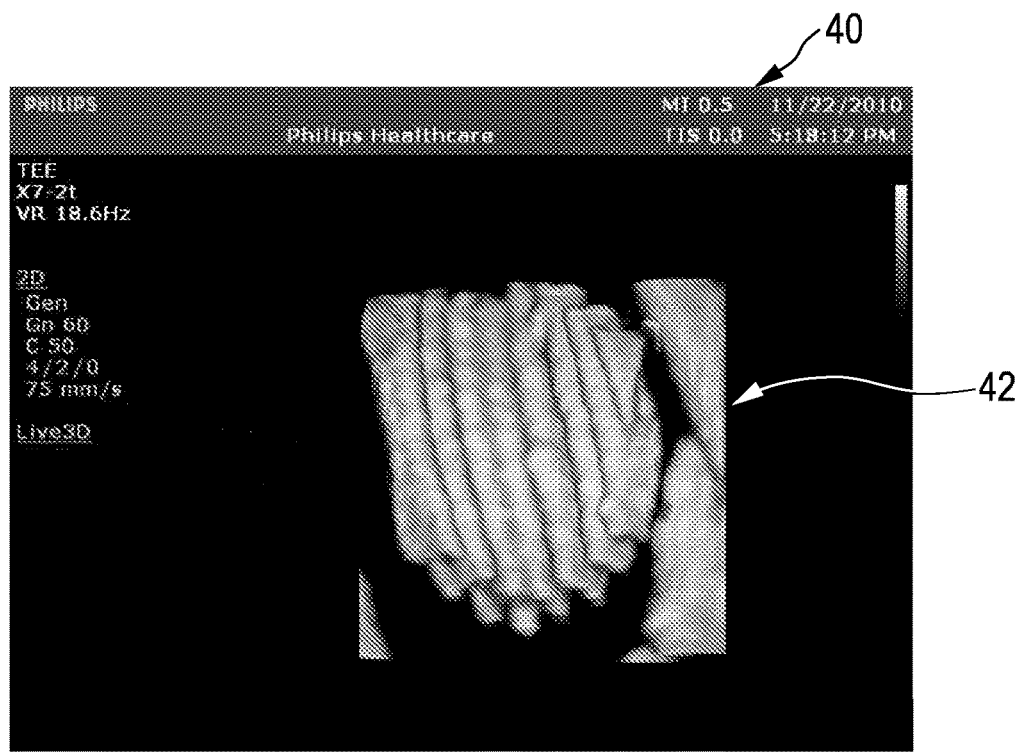
FIG. 4a shows an example of a display with a large region of interest.

FIG. 4a shows a first example display 40 as it may be shown to the user on the display 18 of the ultrasound system 10. On the display, a first large scanned volume 42 is shown as a three-dimensional image of the region of interest.

In this example, the user has set a target volume acquisition rate to 25 Hz (1/seconds), further, the lateral extent is set to 40 degrees and the elevation extent is set to 40 degrees. With these values as user inputs and the above-identified system inputs, the controller 28 can calculate the line density as 1.41 degrees per line via above-identified empirical formula. As this value is within the boundary conditions set via the minimum line density and maximum line density, the actual volume rate of 25 Hz can be maintained as desired.

Figure 4B:
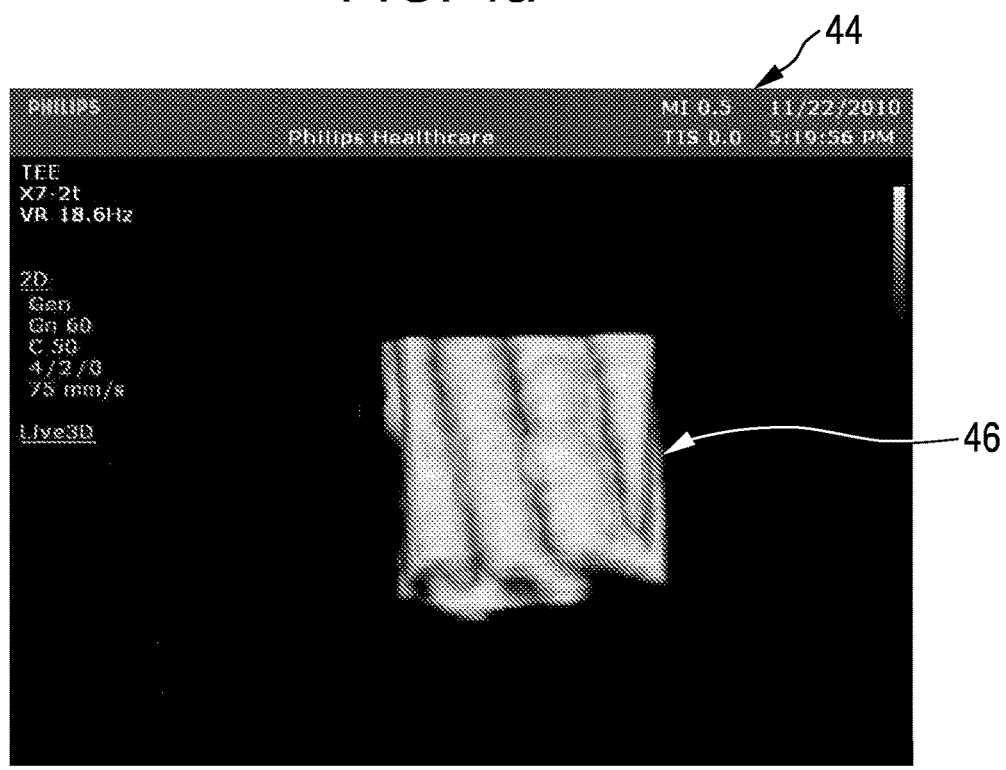

In FIG. 4b a second example display 44 is shown. In this display 44, an image of a smaller region of interest 46 is shown. For example, the user has decided that a particular part of the volume 42 shown in the first example display 40 is of particular interest and may have marked it with a corresponding frame. Alternatively, the user may have directly inputted different values for the lateral and elevation extent of the volume.

In the second example display 44, the desired volume rate may still be 25 Hz (1/seconds) to maintain a live or real time three-dimensional imaging. The lateral extent is set to 22 degrees and the elevation extent is set to 28 degrees. The controller 28 can now calculate the line density to 0.88 degrees per line given the same system inputs as identified above and in the first example. As this line density is within the boundary conditions, the actual volume acquisition rate equals the desired or target volume acquisition rate of 25 Hz. Hence, a live three-dimensional imaging is maintained since the total number of scanning lines 59 across the volume 50 is kept constant. Further, the user automatically has the technical benefit that the smaller region of interest 64 in the example display 44 is acquired with a significantly smaller line density. Hence, the spatial resolution of the smaller region of interest 64 is higher than the spatial resolution of the first larger region of interest 42. However, since the ultrasound system 10 has maintained a constant total number of scanning lines 59, the volume acquisition rate is maintained at 25 Hz. Hence, live three-dimensional imaging is provided to the user after he has picked a smaller region of interest during use. If the user would turn back to the larger volume 42, the same applies vice versa. In particular, even though the user has enlarged the region of interest, the acquisition rate will remain constant.

Figure 5:
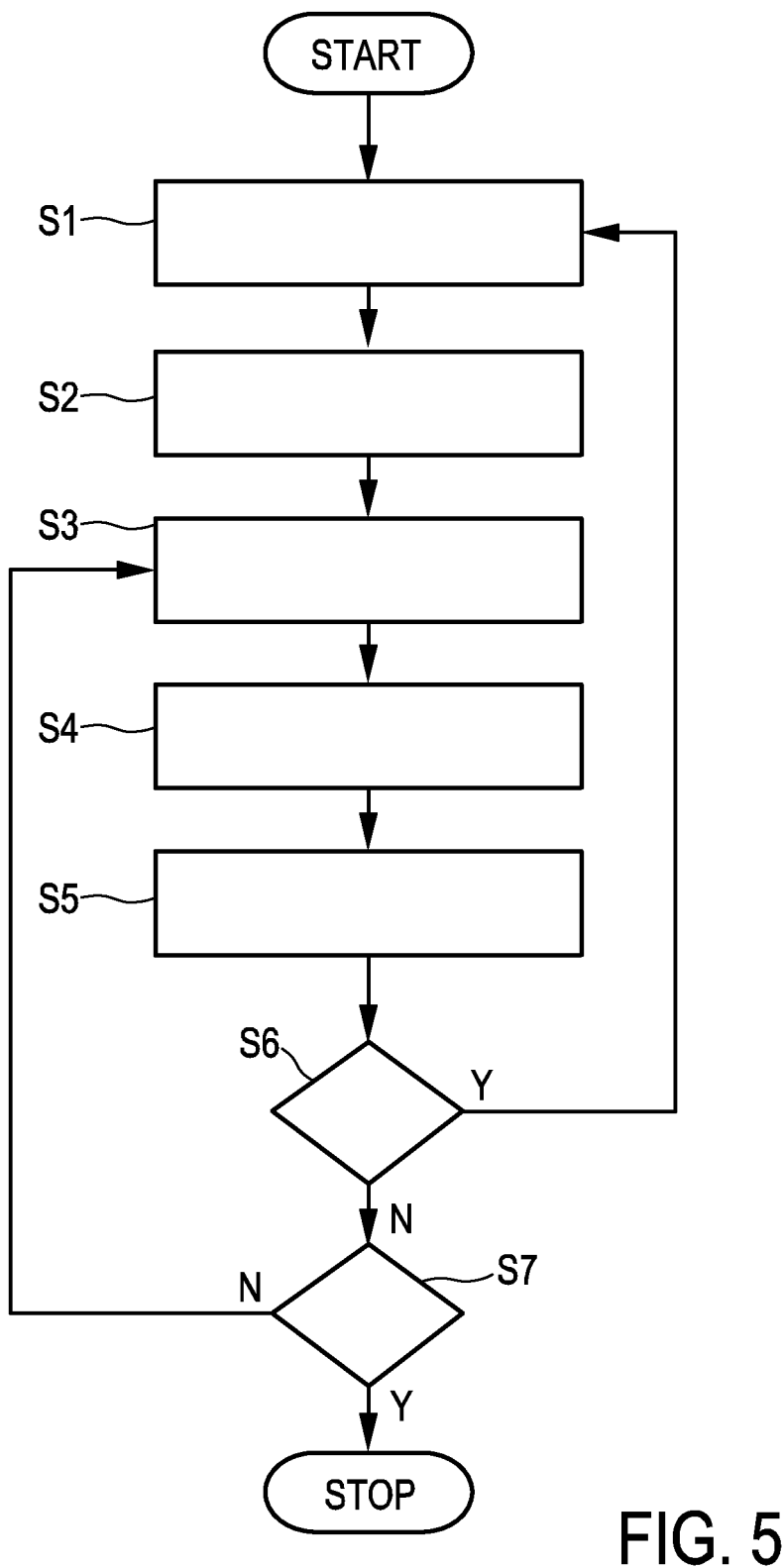
FIG. 5 shows a schematic flow diagram of a method according to an embodiment.

FIG. 5 shows a schematic flow diagram of an embodiment of a method. After the method has been started, the first step S1 is carried out. In this step, the controller receives the parameters determining the size of the volume 50. These parameters are received as user inputs via the input device 20. Further, system inputs have already been made into the ultrasound system 10. System inputs remain constant over a scan of an anatomical site, wherein the user inputs may vary over time during the particular scan. The system inputs are a maximum line density, a minimum line density and a line time. The user inputs are a desired or target volume acquisition rate, a lateral extent of the volume 50 and an elevation extent of the volume 50. Then, in a step S2, the controller 28 calculates and adjusts the line density according to the following formula as laid out above:

$$LD=\sqrt{LE \cdot EE \cdot TVR \cdot LT}.$$

By this, the line density in degrees per line is calculated. Then, in a step S3, the ultrasound system 10 scans the volume 50 along the scanning lines 59 with the transducer array and provides an ultrasound signal. In step S4, the ultrasound signal is processed in the beam former 30 and the signal processor 34 to provide image data. Last, in a step S5, the three-dimensional ultrasound image is displayed using the image data.

Further, optionally, during use and in step S6, it is determined whether the size of the volume to be scanned has changed. In particular, this is the case if the region of interest is changed by the user so that the lateral extent and/or the elevation extent of the volume change. If so, the new user input parameters are inputted into the controller 28 and the line density is recalculated in step S2. The scanning then continues with step S3.

If the size of the volume has not changed in step S6, it may be further determined if the whole scanning process shall be stopped in a step S7. If so, a method ends, if not, scanning continues in step S3.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system for providing a three-dimensional image of a volume, the ultrasound imaging system comprising:
   a transducer array configured to provide an ultrasound receive signal;
   a beam former configured to control the transducer array to scan a volume using a plurality of scanning lines, wherein a number of the plurality of scanning lines is determined based on a preselected scan time, and further configured to receive the ultrasound receive signal and to provide an image signal for the volume;
   an image density controller configured to control the beam former to achieve a target volume acquisition rate, wherein the image density controller is configured to:
      receive data corresponding to the target volume acquisition rate, the preselected scan time, and a size of the volume;
      based on the received data, determine a density of the scanning lines for the volume while maintaining a constant total number of scanning lines for the volume;
      apply a boundary condition associated with a scanning line density to the determined density of the scanning lines; and
      adjust the determined density of the scanning lines by adjusting at least one of the target volume acquisition rate or the size of the volume to meet the boundary condition associated with the scanning line density;
   a signal processor configured to receive the image signal from the beam former and to provide image data;
   an image processor configured to receive the image data from the signal processor and to provide display data; and
   a display configured to receive the display data and to provide a three-dimensional image for the volume.

2. The system of claim 1, wherein the image density controller is further configured to receive the target volume acquisition rate via a user input.

3. An ultrasound imaging system for providing a three-dimensional image of a volume, the ultrasound imaging system comprising:
   a transducer array configured to provide an ultrasound receive signal;
   a beam former configured to control the transducer array to scan a volume using a plurality of scanning lines, wherein a number of the plurality of scanning lines is determined based on one or more preselected scan times, and further configured to receive the ultrasound receive signal and to provide an image signal for the volume;
   a controller configured to:
      control the beam former to achieve a target volume acquisition rate, wherein the controller is configured to receive data corresponding to the target volume acquisition rate, the preselected scan times, and a size of the volume;
      based on the received data, determine a density of the scanning lines for the volume as a function of the size of the volume while maintaining a constant total number of scanning lines for the volume;
      apply a boundary condition associated with a scanning line density to the determined density of the scanning lines; and
      adjust the determined density of the scanning lines by adjusting at least one of the target volume acquisition rate or the size of the volume to meet the boundary condition associated with the scanning line density;
   a signal processor configured to receive the image signal from the beam former and to provide image data;
   an image processor configured to receive the image data from the signal processor and to provide display data; and
   a display configured to receive the display data and to provide a three-dimensional image for the volume.

4. The system of claim 3, further comprising an image density controller configured to receive a lateral extent and an elevation extent associated with the size of the volume via a user input.

5. The system of claim 1, wherein the image density controller is configured to receive the total number of scanning lines as a preset parameter of the system.

6. The system of claim 1,
wherein the image density controller is further configured to adjust the determined density of the scanning lines based on the following empirical formula: $LD = \sqrt{LE \cdot EE \cdot TVR \cdot LT}$,
wherein LD is the density of the scanning lines in degrees per line, LE is a lateral extent of the volume in degrees, EE is an elevation extent of the volume in degrees, TVR is the target volume acquisition rate in hertz and LT is the preselected amounts of time in seconds per line.

7. The system of claim 1, wherein the image density controller is configured to adjust a size of a selection of the volume to meet the boundary condition associated with the scanning line density.

8. The system of claim 1, wherein the image density controller is configured to adjust an actual volume acquisition rate to meet the boundary condition associated with the scanning line density.

9. The system of claim 1, wherein the boundary condition associated with the scanning line density is a maximum boundary condition.

10. The system of claim 1, wherein the boundary condition associated with the scanning line density is a minimum boundary condition.

11. A method for providing a three-dimensional ultrasound image of a volume with an ultrasound imaging system including a transducer array configured to provide an ultrasound signal, a controller, and a signal processor, wherein the volume is to be scanned along a multitude of scanning lines, the method comprises the following steps:
    receiving, by the controller, parameters for determining a size of the volume;
    receiving, by the controller, a target volume acquisition rate;
    receiving, by the controller, a preselected scan time for scanning each respective scanning line;
    determining, by the controller, a density of the scanning lines for the volume based on the target volume acquisition rate, the preselected scan time, and the size of the volume while maintaining a constant total number of scanning lines for the volume;
    applying a boundary condition associated with a scanning line density to the determined density of the scanning lines;
    adjusting the determined density of the scanning lines by adjusting at least one of the target volume acquisition rate or the size of the volume to meet the boundary condition associated with the scanning line density;
    scanning the volume along the constant total number of scanning lines with the transducer array based on the preselected scan time and the determined density of the scanning lines;
    receiving, by the signal processor, an image signal for the volume from the transducer array, processing with the signal processor, the image signal to provide image data; and
    displaying the image data as a three-dimensional ultrasound image for the volume.

12. A computer program product configured to provide a three-dimensional ultrasound image of a volume with an ultrasound imaging system, the computer program product comprising:
    one or more non-transitory computer-readable storage media; and
    program instructions, stored on at least one of the one or more non-transitory computer-readable storage media, to:
    receive parameters for determining a size of a volume;
    receive a target volume acquisition rate;
    receive a preselected scan time for scanning each respective scanning line;
    determine a density of the scanning lines for the volume based on the target volume acquisition rate, the preselected scan time, and the size of the volume while maintaining a constant total number of scanning lines for the volume;
    apply a boundary condition associated with a scanning line density to the determined density of the scanning lines;
    adjust the determined density of the scanning lines by adjusting at least one of the target volume acquisition rate or the size of the volume to meet the boundary condition associated with the scanning line density;
    scan the volume along the constant total number of scanning lines with a transducer array providing an ultrasound signal for the volume based on the preselected scan time and the determined density of scanning lines;
    process the ultrasound signal to provide image data; and
    display the image data as a three-dimensional ultrasound image for the volume.

* * * * *